United States Patent [19]

Cowen et al.

[11] 4,311,570

[45] Jan. 19, 1982

[54] CHEMICAL PROCESS ON THE SURFACE OF A ROTATING BODY

[75] Inventors: Geoffrey Cowen; Philip Norton-Berry; Margaret L. Steel, all of Runcorn, England

[73] Assignee: Imperial Chemical Industries Limited, London, England

[21] Appl. No.: 14,234

[22] Filed: Feb. 21, 1979

[30] Foreign Application Priority Data

Feb. 21, 1978 [GB] United Kingdom ................ 6806/78

[51] Int. Cl.³ .................. B01J 19/08; B01J 19/12; C01B 25/28; C07C 147/06
[52] U.S. Cl. .......................... 204/157.1 R; 204/153 C; 204/157.1 H; 204/158 HE; 204/163 R; 250/527; 422/186; 422/209; 423/312; 423/494; 423/497; 423/604
[58] Field of Search ................ 204/157.1 L, 157.1 R, 204/157.1 H, 158 C, 158 R, 158 HE, 158 HA, 163 R; 250/527; 422/186, 209

[56] References Cited

U.S. PATENT DOCUMENTS

| | | | |
|---|---|---|---|
| 2,132,431 | 10/1938 | O'Brien | 204/158 R |
| 2,507,490 | 5/1950 | Cohen | 204/163 R |
| 3,188,171 | 6/1965 | Ghyssaert | 422/209 |
| 3,227,642 | 1/1966 | Lemelson | 204/157.1 R |
| 3,279,892 | 10/1966 | Lesser et al. | 422/209 |
| 3,347,620 | 10/1967 | Yamashita | 423/608 |
| 3,786,250 | 1/1974 | Huhn | 250/527 |
| 3,993,911 | 11/1976 | Graentzel | 250/527 |

FOREIGN PATENT DOCUMENTS

| | | | |
|---|---|---|---|
| 813869 | 5/1959 | United Kingdom . | |
| 1080863 | 8/1967 | United Kingdom . | |
| 1239383 | 7/1971 | United Kingdom | 204/157.1 R |
| 1282097 | 7/1972 | United Kingdom . | |
| 1333330 | 10/1973 | United Kingdom . | |
| 1540171 | 2/1979 | United Kingdom . | |

Primary Examiner—Howard S. Williams
Attorney, Agent, or Firm—Cushman, Darby & Cushman

[57] ABSTRACT

A wide variety of chemical processes using thin films of reactants are carried out on the surface of a body rotating at high speed and the products are readily isolated (for example as fine particles or fibres) by using centrifugal force to fling the products from the rim of the body.

9 Claims, 9 Drawing Figures

CHEMICAL PROCESS ON THE SURFACE OF A ROTATING BODY

This invention relates to chemical processes involving a thin-film reactor.

It is known that in many chemical processes the reactants advantageously are spread as a thin film over a surface and in this way reactions may be carried out with minimal heat transfer problems. Various mechanical devices have been used for spreading and maintaining reactants in thin films; usually these are rotary devices for example blades or vanes co-operating with a static surface or rollers running past a static doctor blade.

We have now found that reactants which are in liquid or other fluent form may be spread, mixed and reacted as a thin film on a surface which is rotating at high speed, without the need for an extra mechanical member to spread or maintain the thin film.

Thus the surface of a body rotating at high speed may be made the basis of a chemical reactor for a continuous chemical process.

According to the present invention there is provided a chemical process wherein a fluent reactant medium is continuously supplied to a surface of a rotating body the surface being a surface of rotation coaxial with the axis of rotation of the body so that forces generated by the rotation of the body cause a film of the reactant medium to move across the surface from the supply zone to a discharge zone axially remote from the supply zone, the process being characterised in that the rate of supply of the medium and the speed of rotation of the body are regulated such that (i) chemical reaction occurs in the film of the said medium and the product of this reaction is produced during the movement of the film between the supply and discharge zones and (ii) the said product is continuously discharged from the surface of rotation at the discharge zone by using the centrifugal force of the rotating body to fling the product from the surface into the surrounding atmosphere.

The reactant medium may consist of one or more reactants in liquid form, a fluent slurry of solid and liquid reactants, any reactants in a liquid diluent, a foam or free-flowing dry powder. Continuous supply of the reactant medium includes intermittent supply frequently administered for a period of time for example pulsed sprayed or dropwise addition of reactants to the surface of the rotating body. The chemical reaction, which may be organic or inorganic, includes reactions of gas, liquid or solid present in the reactant medium. The medium should be capable of spreading and moving over a surface under the influence of suitable forces, the extent and speed of such movement obviously being governed inter alia by the viscosity and density of the medium and the surface tension and surface friction between the medium and the surface. In a preferred embodiment the reactant medium consists of fluids only and contains no solid phase before chemical reaction occurs on the surface.

The rotating body having the coaxial surface of rotation may be for example a solid body, a hollow body or a shaped vessel; the surface of rotation accordingly may be either an external and/or an internal surface of the body. Examples of suitable bodies are cylindrical vessels and conical vessels (especially bowls, cones or diabolos) having surfaces of rotation with a central axis and at least part of that surface being inclined to the axis at an angle of less than a right angle. In such vessels the supply zone of the surface and the discharge zone will be axially displaced with respect to each other. On a flat disc spinning perpendicular to the axis of rotation there could be no axial displacement but if the rotating body comprises a flat disc or annulus in combination with a cylinder or cone as shown in FIG. 2, the supply zone could be on one portion e.g. the cylinder or cone at A and the discharge zone could be on another portion e.g. the disc or annulus at B and these zones would be axially remote from each other.

Thus a variety of shapes are possible for a body useful in this invention, those preferred having an internal surface of rotation which both varies in diameter and extends in an axial direction (X . . . X) The bodies especially preferred are cups and bowls comprising surface portions which are substantially parallel to the axis of rotation and which may usefully have a flared rim which acts as the discharge zone. A particularly preferred shape for the profile of the surface is a parabolic curve which makes only a small angle with the axis near the rim. The rotation of the body will generate forces which will operate on a liquid supplied to the surface, forces which include mainly a centrifugal force operating radially from the axis of rotation and a rotary force operating circumferentially at the surface of rotation. The rotary force overcomes inertia of the reactant medium on the surface and imparts a rotary motion to it, due to frictional drag between surface and medium. If the rotating body dips into a reservoir of liquid (for example the reactant medium may be supplied to the surface in this manner) the rotary force will impart a stirring or shearing action to the liquid. This, depending on the viscosity and surface tension may cause the liquid to climb out of the reservoir as a consequence of the Weissenberg effect, and so spread on the outside (or inside) surface of rotation of the rotating body.

Without prejudice to the process of the present invention we believe that the centrifugal force operates in a direction away from the axis of rotation but perpendicular to that axis, and thus will tend to fling the reactant medium off an exterior surface of rotation unless it is held by other forces, for example, cohesion, adhesion, surface tension, etc. When these forces operate, thin-spreading films can be obtained on an external surface of rotation. However, we have a preference for conducting this process on an internal surface of rotation i.e. a surface facing towards the axis of rotation for example the internal surface of a rotating cup or bowl. The centrifugal force operating outwardly from the axis in vessels of this type will tend to spread the reactant medium on the surface and cause it to form a thin uniform film over the whole surface of the vessel and will still do so with highly viscous materials. If the reactant medium is supplied to the bottom of a rotating cup or bowl the forces generated by the rotation, especially the centrifugal force, will form a film which will spread outwardly from the axis of rotation and move as a uniform film or layer towards the rim of the cup or bowl from which it will be discharged. The movement towards the rim of the cup or bowl is a movement which is at least partially in an axial direction, i.e. upwardly if the bowl is upright with a vertical axis which has advantages for the supply of reactant to the bowl by gravity. However, the bowl may be inverted and then the motion towards the rim will be downwardly: this latter arrangement can have advantages for the collection of products which fall under gravity after discharge without interference with the rotating mechanism.

The axis of rotation may be other than vertical although this is the most convenient and most preferred direction for the axis of rotation in this invention. The rotary propulsion may be applied to the body by a shaft from either end of the axis (e.g. from the top or the bottom if it is a vertical axis) or by other means e.g. turbopropulsion.

The magnitude of forces generated by the rotation of the body which operate upon the reactant medium to move it across the surface will be dependent upon many factors which include the speed of rotation and the radius of the surface of rotation. The greater the speed of rotation and the greater the radius the larger is the centrifugal force. It will be evident that the radius will not be constant over all the surface for those bodies not entirely cylindrical and thus the centrifugal force operating on the reactant medium may, for example at a region of larger radius, increase to a magnitude great enough to overcome other forces such as adhesion and surface tension operating to hold the reactant medium on the surface. Thus at a predetermined discharge zone, for example a part of the surface having a larger radius or terminal parts of boundaries of the surface, the medium is flung away from the surface into the surrounding atmosphere by means of the centrifugal force.

For the chemical process of the invention to be carried out a film of the reactant medium will have been chemically changed at least in part to the product of the process before it reaches the discharge zone and is separated from the surface. Thus the time for the passage of a portion of the reactant across the surface from the supply zone to the discharge zone (which may be termed the residence time) should be arranged to be sufficient for the desired chemical reaction to proceed, to completion, preferably, but not so long as to cause byproducts to be formed on the surface. For the most efficient operation of the process the reactant medium will have substantially fully reacted to form a product by the time it reaches the discharge zone. This may be achieved by the careful control of the various parameters available including the speed of rotation, the size and shape of the rotating body or of its surface of rotation.

The rate of supply of reactant medium to the surface of rotation is also a factor which affects the rate of reaction. The faster the supply the thicker is the film formed on the surface assuming other factors such as the viscosity and speed of rotation are not varied. However, a thicker film in certain circumstances may require a longer residence time in order to achieve an appreciable conversion to product before being discharged. Alternatively a highly exothermic reaction may proceed faster in a thicker film and then a shorter residence time will be necessary or it may be preferable to operate with a thinner film. Therefore a careful balance between all the factors should be sought in order to operate the process efficiently.

The product may be discharged from the surface either as a continuous sheet (which may by cooling or evaporating change from the liquid to the solid state) as fibres or filaments or as an atomised spray which if desired may be collected in bulk form as either a liquid or powder. It is convenient to place collecting apparatus around the rotating body to receive the product, the apparatus taking whatever form is appropriate to the type of product obtained. The process of the invention is particularly advantageous for the production of either insoluble polymeric products in particulate form or in fibre form for example either long filaments or staple fibre especially a tangled wool, tow or non-woven fabric of fibres may readily be obtained from the discharge zone in many polymeric reactions.

If a body is rotating and liquid reactants are fed continuously to the surface of the body the movement of the liquid across the surface to the discharge zone and the discharge of products (and any excess reactants) will continue whilst the body is rotating. It may be necessary to apply lengthy and perhaps tedious trial and error adjustments in order to arrange the balance of parameters for optimum yield of product but it may be seen that a continuous chemical production process may be conducted with the simplest of apparatus. The process has many advantages. The reaction takes place in a thin film and therefore contact with gas in the surrounding atmosphere or contact with solids on the surface is rapid and complete. Heat transfer problems are minimised because there is immediate and virtually complete contact by all portions of the reactant medium with a heat transfer surface either the gaseous interface with the outer surface of the film or the contact of the underside of the film with the rotating body itself. Heat may be imparted or taken out of the film quickly and easily by either route and additionally if desired the film could be heated in a variety of ways e.g. infra-red and microwave radiation and dielectric or eddy current heating. It is especially advantageous if the rotating body itself has a low mass, and hence a low thermal capacity, and also a high thermal conductivity, for example a thin-walled bowl of good conductivity is especially preferred.

A further advantage of the process is that unstable or intermediate products and products capable of further reaction may be isolated rapidly and prevented from further reaction or decomposition by their rapid discharge from the surface by centrifugal force. They are thereby removed from the reaction zone and thus also from the influence of factors which cause the reaction to take place and which might cause the products themselves to decompose. Solvent and any volatile by-product is removed quickly by evaporation in the atmosphere after discharge.

The reactor used in the present invention is superior to other thin-film reactors in that the film is formed and transported solely by means of the rotation of the body. The rate of throughput of reactant and/or product may be increased simply by increasing the speed of rotation: there is no need to change the apparatus. Also other factors may be altered without changing the apparatus, factors such as the nature or viscosity of the reaction medium, the gases, liquids or solids reacting with the medium and the length of time or other conditions of the reaction. Therefore a large variety of different chemical reactions may be carried out in the same apparatus, for example homogeneous or heterogeneous reactions to make monomeric or polymeric products; reactions which may include, for example, polymerisation by opening double bonds or condensation processes and redox reactions using gaseous oxygen or hydrogen.

The process of the present invention offers advantages for many different types of chemical reaction particularly for those types of reaction which are difficult to carry out in conventional vessels, pipes or columns. For example reactions involving large thermal changes may be readily controlled in a thin film of reactant on the surface of a rotating body. Therefore the type of reactor used in the present invention gives special advantages over other types of reactor when a very fast exothermic or endothermic reaction is carried out (for example one which has a reaction half-time of less than 100 milliseconds) because it provides very efficient transport of reactants across the surface. It is easy to melt solids in powders or in lump form on the surface of a heated rotating vessel and then the molten liquid travels over the surface from underneath the mass of solid.

If a solid product is formed in the reaction for example from a reactant medium which is a melt or a very concentrated solution the rotating body will transport the solid product to the discharge zone without difficulty and the solid may be readily isolated in a dry form for example upon radial or tangential discharge into the surrounding atmosphere as particles or fibres.

The transport of very viscous reactant media is possible and the process is especially advantageous over conventional processes when reaction products are formed which markedly increase the viscosity of the reaction media. The adequacy of the force transporting the reactant medium across the surface may be assessed during the process and if it is found to be inadequate when chemical reaction is proceeding the speed of rotation may be increased so that the product reaches the discharge zone in a convenient time and is satisfactorily discharged. Such instant control is not normally possible in other reactors. For viscous products the discharge process of flinging from the rim is more efficient than conventional methods of separation and collection.

When a gaseous product is formed during the reaction and removal of the gas is desirable the thin film of reactant medium moving across the surface of the rotating body provides ready disengagement of the gas without foaming or pressure-blocking of the system. Conversely reactant gas may be rapidly absorbed into the thin film and even rapid reactions, involving either absorption or desorption of gas, (for example those wherein the reaction half-time is less than 2 minutes) are especially suitable for operation by the process of this invention. It is particularly advantageous when the reactants and/or products are viscous liquids: gases may be mixed or removed faster than by conventional processes.

In these above types of chemical reaction and others hereinafter described the process of the present invention may offer unique advantages of ease of control, and handling of materials, not found in any other chemical process or chemical reactor.

Changing from one chemical reaction to another is also easy because cleaning problems are minimised by the self-cleaning action of the apparatus: since the product and excess reactant are discharged in general from a smooth surface, and there is almost complete discharge and minimal residues remain to be cleaned away before a different reactant medium is introduced to the surface of the rotating body for re-use in a process to produce a different product. During the continuous operation for one product the apparatus does not allow build up of by-products which may be formed: they are pushed through with products. The invention is particularly applicable to the continuous production of a polymeric product by a condensation process wherein the rapid evolution of a volatile product, (e.g. water) enables the process to be completed in the minimum time and to the production of a gelled or cross-linked polymeric product in finely divided form for example made by the addition of cross-linking or gelling agent with a solution or melt of the polymer on the rotating surface.

In U.S. Pat. No. 3,161,710 a process for the production of linear polyesters is described in which the reactants are present as a thin film spread on a moving tape or conveyor belt: a film from $10^{-5}$ to $10^{-3}$ inches thick is stated to be necessary. In the process of the present invention we are able to produce and transport films of the reactants within the ranges of thicknesses quoted in the U.S. patent. Therefore all the advantages of the thin film reaction (particularly increased rate of production of a high quality product) may be realised by the process of our invention coupled with the ability to spin staple-fibre or longer filaments of the polyester product in the same apparatus immediately the polymer is formed. A low partial pressure of volatile by-products (e.g. in this case water vapour) is desirable and this is readily achieved in our process by enclosing the rotating body in an evacuated chamber for example a chamber enclosing an atmosphere at a pressure in the range from 10 mm mercury down to 0.01 mm mercury. Disengagement of vapour from liquids is very quick and efficient; the acclerating force operating on the reactants helps to collapse bubbles and prevent any troublesome foaming.

A multi-stage process may be operated by arranging for example a series of rotating bodies, preferably rotating about the same axis and also conveniently from the same drive-unit. The product from the first body is discharged to the surface of the second where the second stage of the process is conducted and so on to the third or other successive bodies. One may arrange a different set of conditions for each stage e.g. temperature, concentration of gas, etc. For example the condensation of ethylene terephthalate is suitably conducted in several stages wherein the intermediate products include the di-ester of ethylene glycol and terephthalic acid and the dimeric oligomer containing two molecules of each reactant. Such a reaction is ideally suited to be carried out by a process according to this invention because thin films speed up the reaction and the products and intermediate are viscous liquids and it is imperative that they are moved away continuously from the reactants at each stage by powerful forces. Such forces are continuously available in the process of this invention.

The invention employs rotation at high speeds and by "high speed" as used herein we mean speeds in excess of 500 rpm. The forces operating on the reactant medium causing it to move on the surface do not depend solely on the speed but they depend also on the physical dimensions of the rotating body e.g. the radius and angle the surface makes with the axis of rotation. Thus any choice of speed of rotation must be selected bearing in mind the size and shape of the surface of the body which is rotating. The centrifugal force may be measured by the acceleration of the film on the surface of rotation. Our process works effectively when accelerations of at least 100 m sec$^{-2}$ preferably at least 400 m sec$^{-2}$ are present on the surface of rotation.

The speed of rotation may vary over a wide range, in general speeds from 500 rpm up to 100,000 rpm may be used but the range which is most useful is from 1000 rpm to 30,000 rpm. The motive power for the rotation and the design of rotor bearings and rotating seals and feeds for the rotating body may be those known conventionally in engineering science.

The surface of rotation on which the product of the process is formed is preferably an "unbroken" surface by which we mean a surface which is circumferentially continuous without holes, gaps or ports or other discontinuities, but the surface may be ridged, undulating, convoluted or otherwise patterned if desired in order to improve the movement of the reactant medium and/or the product for example to aid the mixing of components.

The edge or rim of the body may be fluted or otherwise patterned in order to improve the discharge of product in any desired form.

The surface of rotation on which the chemical process of this invention takes place may be usefully an inert surface for example of glass, plastic, ceramic, metal, or composite materials especially chemically resistant metals e.g. stainless steel, nickel, titanium and tantalum are preferred. Alternatively metals coated with chemically resistant surface materials for example glass, silicone resins or polytetrafluoroethylene are useully employed. Flexible films may be used as materials for the rotating body which would be rigidified by the centrifugal force operating when they are rotating and they may constitute a cheap form of bowl or cylinder on which the process of this invention may be conducted.

With the materials mentioned above, the surface of the rotating body takes no part in the chemical reaction but it may be advantageous to conduct the process of the invention on a surface which reacts chemically with the reactant medium. Most usefully the surface may be treated with a catalyst for the chemical reaction in question and in this way the residence time necessary to obtain complete reaction and a high yield of product may be reduced and the throughput of the process thereby increased. For example the surface of the reactor may be coated with an adherent porous material (for example high area silica or alumina) and the surface coating may itself act as a catalyst or constitute a substrate on which catalytic materials may easily be deposited or adsorbed.

For example if a supported nickel catalyst (e.g. reduced nickel oxide) is attached to the surface of a bowl, the bowl set rotating and nitrobenzene and hydrogen passed into the bowl which is maintained at 150°–200° C. the nitrobenzene may be reduced to aniline as it flows over the catalytic surface. Water is evolved as steam and the reduction product aniline as a liquid spray from the rim of the bowl. The advantage in the present process over conventional processes is that the cyclohexylamine which tends to be produced by further reduction of the aniline is minimised by the rapid removal of products from the surface carrying the catalyst. Thus according to another aspect of the present invention there is provided a reactor for a chemical process as herein specified comprising a body capable of rotation at high speed about an axis having a coaxial surface of rotation coated with a substance which comprises a heterogeneous catalyst for the chemical reaction to be carried out in the reactor, the surface terminating in a circular boundary from which the product of the reaction may be discharged.

Many chemical processes are initiated either thermally or with a catalyst and it has been described hereinbefore how the process may be conducted advantageously on a surface of rotation spinning at high speed. Some chemical reactions are initiated or conducted photochemically e.g. by UV light but hitherto photochemical processes have not been industrially successful because of the difficulty in obtaining a high light intensity uniformly throughout a large mass or over a large area of surface of reactant. In the process of the present invention this problem is minimised because although the reactor is spread over a surface area the surface is rotating at high speed and therefore a high intensity beam of light may be used and focussed upon a small region of that surface. The fact that the surface is rotating at high speed and carries the reactant medium also on a rotary path allows a large area to be illuminated almost instantaneously by the light beam. In addition the movement of the reactant medium in an axial direction or with an axial component to the direction insures the illumination of an even greater mass of reactant by the light beam. The reactant medium is present on a surface which may easily be illuminated without difficulty therefore problems often encountered in photochemical processes (e.g. fouling window materials) are minimised. Advantageously the beam of light may be generated by a laser which is well known to produce a very high intensity, pencil beam of coherent light very well defined in wave length. All these factors will help the operation of specific photochemical processes in this apparatus which could not be efficiently carried out in other reactors.

According to a further aspect of the present invention there is provided a novel chemical reactor comprising a body capable of rotating at high speed about an axis of rotation having a coaxial surface of rotation extending both circumferentially and axially and a source of radiation adapted to direct a beam of radiation on to the said surface of rotation. It is preferred that the said source is a laser source, especially a laser source providing a continuous beam of radiation. The axis of rotation is preferably a vertical axis whenever tubes or bowls are used where it is inconvenient to have a bearing at both ends.

The pencil beam of a laser source may usefully be focussed onto a portion of the discharge zone (for example the rim or flange of a rotating cup or bowl) and may be used to modify the product as it is discharged. For example a polymeric product may be cross-linked thereby and thus stabilised in a desired form, especially a fibrous or particulate form, very conveniently and uniformly without the need for a subsequent treatment. Altenatively the source may emit high energy radiation, for example shortwave electromagnetic such as X rays or γ-rays or high energy particles such as electrons α-particles or ion beams may be used if desired to conduct the process.

Amongst the reactions which are usefully conducted by the process hereindescribed are biological or biochemical reactions especially those which require a plentiful supply of oxygen for example reactions with or in living cells: also enzymatic reactions may be conveniently controlled in a centrifugal reactor as hereindescribed.

Figure 1:
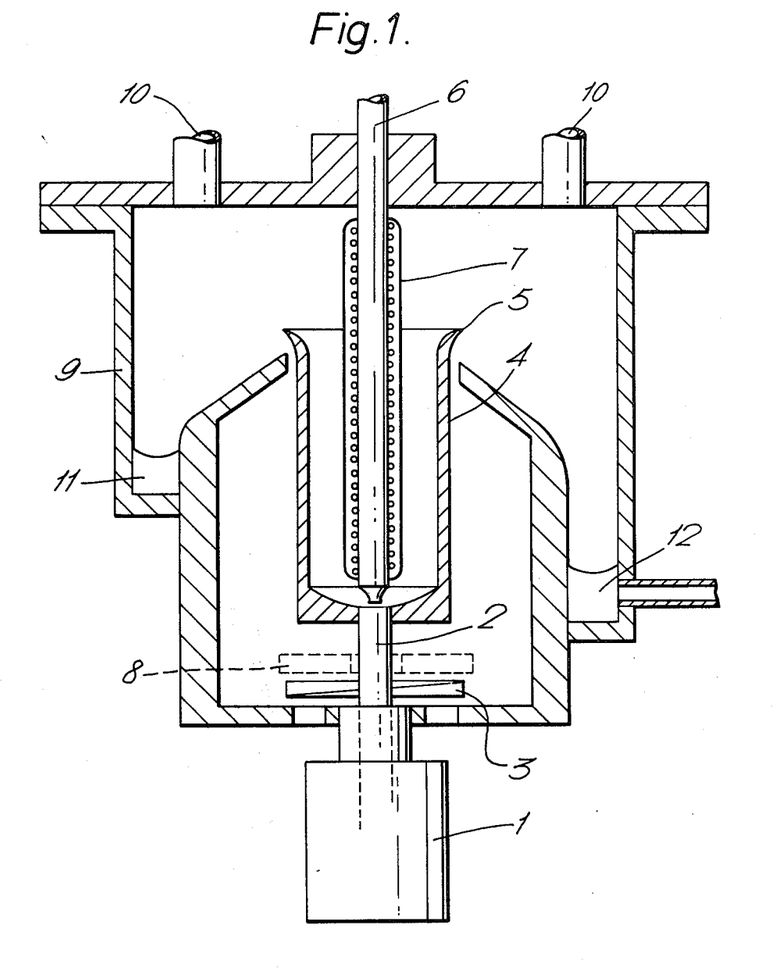
FIG. 1 is a vertical sectional view of an apparatus embodying the principles of the present invention.
Figure 2A:
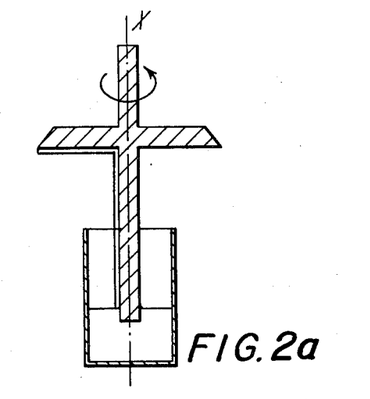
FIGS. 2a, 2b, 2c, 2d, 2e and 2f are vertical sectional views of six different shapes suitable for the body of revolution.
Figure 2B:
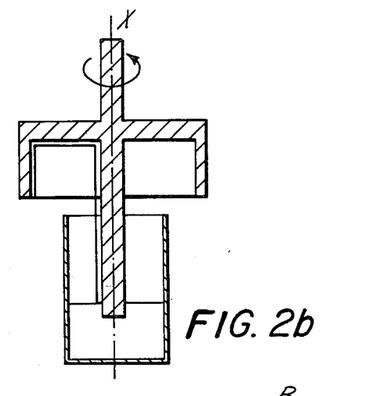
Figure 2C:
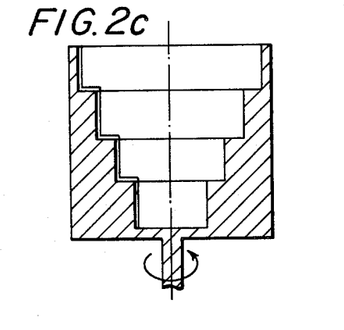
Figure 2D:
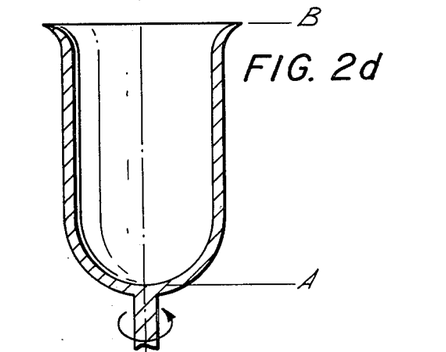
Figure 2E:
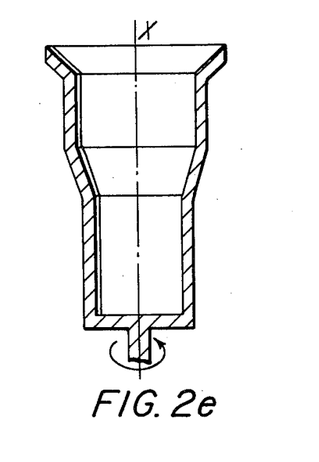
Figure 2F:
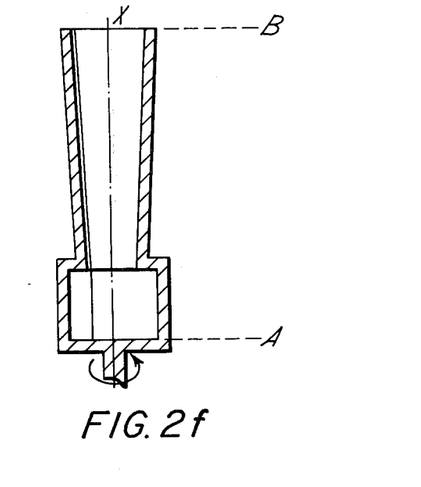

An example of an apparatus suitable for carrying out the continuous process of the present invention is illustrated diagrammatically in FIG. 1.

A variable speed electric motor (1) has a vertical drive shaft (2) connected to the centre point of the base of a circular bowl (4) having a flanged rim (5). Underneath the base of the bowl and connected to the drive shaft is a fan with impeller blades (3) situated below a heater (8). A tube (6) for the delivery of liquids to the bowl has a heatable insulating jacket (7). The outlet of the tube is directed near to the centre point of the interior of the bowl. If more than one liquid is required to be added independently to the bowl the tube (6) may be duplicated. A circular housing (9) with vents (10) at the top surrounds the bowl and is shaped into moat (11) which drains fluent materials towards a collection point (12).

In operation when the bowl is rotating at high speeds for example at 1,000–5,000 rpm liquid reactant is run down tube (6) and when the liquid contacts the base of the bowl it spreads in a thin film over the whole of the base of the bowl. Alternatively, liquids may be sprayed in by pressure or by centrifugal force. Liquids may also be introduced through the drive shaft (2) if this is a hollow tube. As fresh liquid contacts the base, the liquid first climbs up the sides of the bowl as a uniform thin film until it reaches the rim (5). The centrifugal force which operates to move the liquid up the sides of the bowl also causes the liquid to be flung from the rim either as a sheet of liquid which breaks up into droplets or a fine mist spray or as ligaments which stabilise into fibres or filaments.

Two liquids may be run simultaneously into the bowl both through the same tube or through independent tubes which may have a concentric axis.

The liquids are caused to react on the bowl and form a product. If the product is soluble in the original liquid or if the product is itself a liquid the foregoing explanation applies to the product as much as to the reactant. One cannot tell precisely where on the surface the reactant turns into product but when appreciable reaction occurs on the bowl it is mainly product which is discharged from the rim of the bowl. As the product is formed it travels with any unreacted (and possibly still reacting) reactant medium up the sides of the bowl towards the rim. If it is observed that the reactant medium and/or the product are not travelling fast enough to be discharged in the desired form the speed of rotation may be increased. Conversely if it is observed that there is insufficient yield of product and the reactant medium requires a longer time on the surface of the bowl, either the speed of rotation or the rate of supply of reactant medium may be decreased. The reaction operates continuously until the supply of reactant ceases. When this happens a bowl will clear or clean itself whilst it is still rotating if the diameter of the surface is arranged to increase continuously towards the discharge zone.

The impeller (3) which is an optional attachment but not an essential of the process, allows air to be directed around the sides of the bowl (4) whilst the bowl is rotating. The air may be warm air (heated by heater 8) to heat the bowl or cold air (drawn from outside the housing) to cool the bowl. The air directed by the impeller also affects the temperature of the product because the air in the immediate vicinity of the rim (5) is provided by the air directed upwards by the impeller. However, other air currents may be used to counteract the effect of the impeller on the product for example, downwardly-directed draughts from above the bowl or upwardly-directed draughts further from the bowls' circumference; the temperature of such draughts being chosen to obtain the best physical form for the product of the process.

If two liquids of different density are present the centrifugal force may cause layering of the liquid film, the more dense liquid tending to be forced nearer to the surface of rotation. The liquids may travel towards the rim of the bowl in layered form and be discharged at different angles and collected separately: thus a separation of products from reactants or from catalysts is possible merely by means of the forces generated by the rotation. Free-flowing or free-running solid powders for example, calcium carbonate or polypropylene may be added directly to the internal surface of the rotating body and caused to travel over the surface as a uniform layer of particles which are wet or dry as desired. They may be reacted with gas, liquid or even another solid powder or they may merely be caused to react by thermal or photo initiation. Alternatively liquids may be supplied to the surface on which a solid powder is running, whereupon the liquid will be intimately mixed with the solid and reaction between liquid and solid thereby made possible. In this way a rotating bowl may be used as a thin layer fluidised bed. For this purpose a cylindrical surface is not ideal but an outwardly sloping conical or parabolic surface is preferred.

The invention is illustrated by the following examples in which parts and percentages are by weight unless otherwise stated.

EXAMPLE 1

Phthalic anhydride and maleic anhydride in equimolar proportions were dissolved in an excess of propylene glycol at a temperature of 50° C. The solution was cooled to room temperature and immediately passed into a tube which delivered the solution to the surface of a stainless steel bowl of dimensions 4.5 in. diameter and 4.0 in. high maintained by hot air at a temperature of 200°–250° C. and rotating about a vertical axis of a speed in the range of 2000–2800 rpm.

A film of this solution was produced on the sides of the bowl where reaction occurred to form an unsaturated polyester resin, the exact properties being dependent on the speed of rotation and the precise temperature of the bowl. The resin was discharged from the rim of the bowl in the form of a sheet of liquid which broke up into droplets of liquid and these were collected on a cylindrical sheet of aluminium foil set at a distance of 18 in. from the rim of the rotating bowl.

The viscosity of the resin produced at 250° C. was measured as ca. 30 poises on a "cone and plate" viscometer at 25° C. and the resin produced at 200° C. had a viscosity of 15 poises at 25° C. Reaction was run continuously for two hours and stopped merely by ceasing the flow of dissolved reactants.

EXAMPLE 2

A mixture of three solid reactants namely
(i) 44'dihydroxydiphenyl sulphone
(ii) anhydrous potassium carbonate
(iii) 44'dichlorodiphenyl sulphone in equimolar proportions were heated with an excess of diphenyl sulphone solvent until all the sulphone components were thoroughly mixed into a melt containing suspended potassium carbonate. The melt was passed down a heated tube maintained at ca. 135° C. on to the surface of a rotating bowl. The substituted sulphones reacted together on the surface of the bowl and semi-solid particles of a polyether sulphone having a formula were obtained on a stationary collecting surface set around the periphery of the bowl. The product was removed from the collecting surface continuously by a scraper.

EXAMPLE 3

Solid hexamethylene di ammonium adipate (mpt. 183° C.) commonly known as "nylon salt" was fed to the surface of a bowl rotating at ca. 3000 rpm maintained at ca. 280° C. The powder melted to a liquid on the surface and the liquid was transported by the sides of the bowl and thereby converted to nylon 66 polymer. The polymer was discharged by centrifugal force from the rim of the bowl into the atmosphere as molten particles which solidified into a granular form of the polymer as they cooled: granules were continuously collected as they fell under normal gravity into a collector beneath the rotating bowl.

EXAMPLE 4

Figure 3:
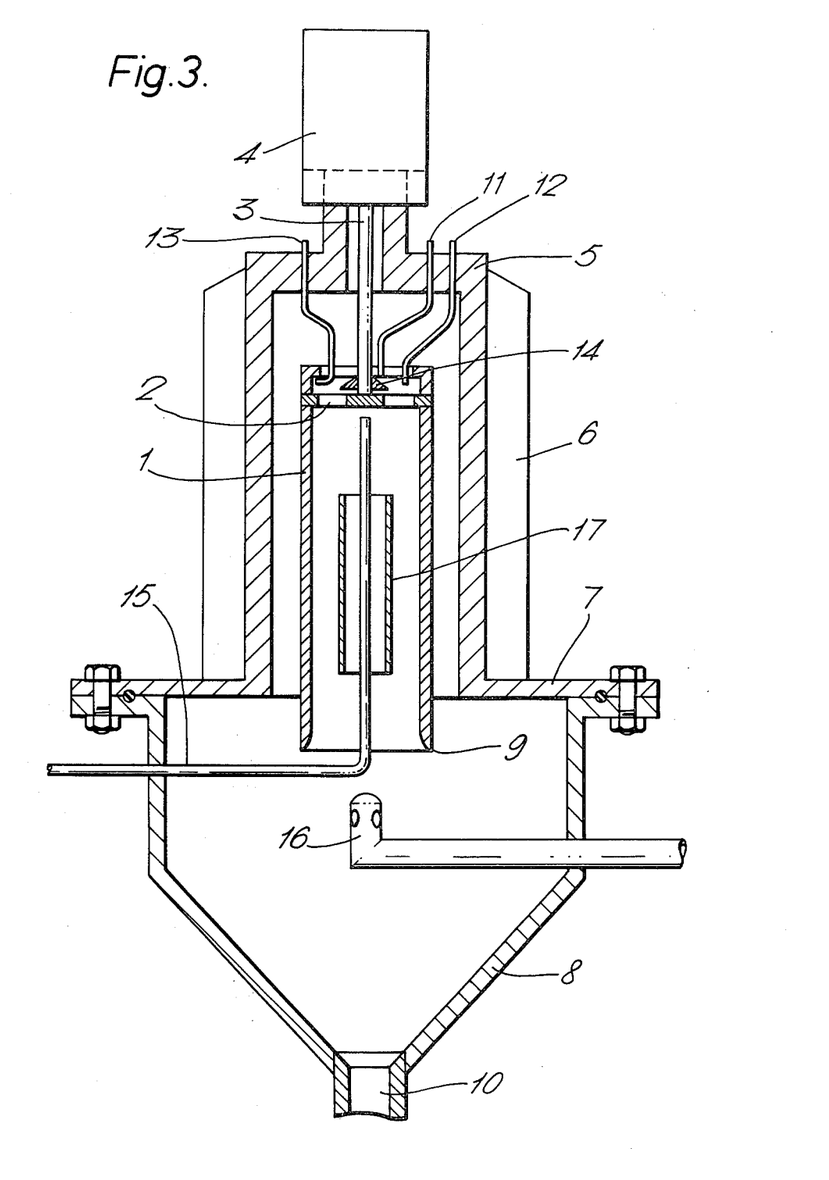
FIG. 3 is a vertical sectional view of a second embodiment of an apparatus in accordance with the invention.

Chlorinated polyisoprene was produced in an apparatus shown diagrammatically in FIG. 3. A liquid low molecular weight polyisoprene was supplied by pipe 11 to the centre of the drive shaft (3) and sprayed from cone 14 out onto the surface of the tube (1) which was capable of being rotated about a vertical axis by the motor (4). Chlorine gas was passed into the apparatus by means of entry pipe 15 while the inside of the tube was irradiated by the ultra violet lamp (17). The cabinet (5) and collector (8) enclosed the working parts, safely contained the poisonous chlorine gas and was shaped to allow the chlorinated polymer product flung by centrifugal force from the rim (9) of tube (1) to drain from outlet tube (10).

EXAMPLE 5

The reaction of anhydrous 4,4'-bipyridyl with 1-chloro-2,4-dinitrobenzene to produce N-(2,4-dinitrophenyl)4,(4'pyridyl) pyridinium chloride; i.e. the monoquaternary salt This reaction is an example of an exothermic reaction in which the product is insoluble in the reactants and and crystallises rapidly from the reaction mixture. Conventionally, the reaction is carried out in the presence of an inert solvent in which both reactants are soluble, but the product, preferably, is insoluble. The presence of the solvent in conventional reactor vessels facilitates control of the reaction exotherm (by refluxing) and also reduces stirring problems. However, this reaction is most efficient at high reactant concentrations and becomes less efficient in the presence of increasing amounts of solvent.

The conditions usually employed are as follows: Stoichiometric equivalents of the reactants are mixed and melted at 70°-80° C. The mixture is heated to 90° C.-95° C. whereupon an exothermic reaction ensues. This is difficult to control since the product rapidly precipitates as a crystalline solid and the sludge formed inhibits and often prevents efficient stirring. If stirring ceases the product forms as a very hard cake and the highly exothermic reactions still occurring at the centre of the mass cause tarry byproducts to be produced. A moderating solvent has been used to facilitate stirring and thereby aid the control of this exothermic reaction. The solvent must be one in which the mono-quaternary salt precipitates to prevent formation of diquaternary salt, and although the presence of an excess of solvent does facilitate stirring to control the exotherm there are some disadvantages. The reaction rate is reduced because it is concentration dependent and the solvent must be removed from products and recovered if an efficient process is to be operated.

In order to conduct the reaction satisfactorily in the absence of solvent without the occurrence of tarry byproducts the reactants were melted together at 75° C.-90° C. and introduced to the surface of a bowl rotating at ca. 5000 rpm and maintained at a temperature of 135° C. The required product was formed whilst the reactant mixture moved rapidly under centrifugal force as a thin film up the sides towards the rim of the bowl during which time crystalline solid particles began to form. The crystalline particles were flung from the rim of the bowl and collected on the vertical wall of a hopper surrounding the rim of the bowl. The products collected were purified by washing with acetone and recrystallised in methanol. Yields in excess of 70% theoretical have been achieved employing the conditions illustrated above.

EXAMPLE 6

Figure 4:
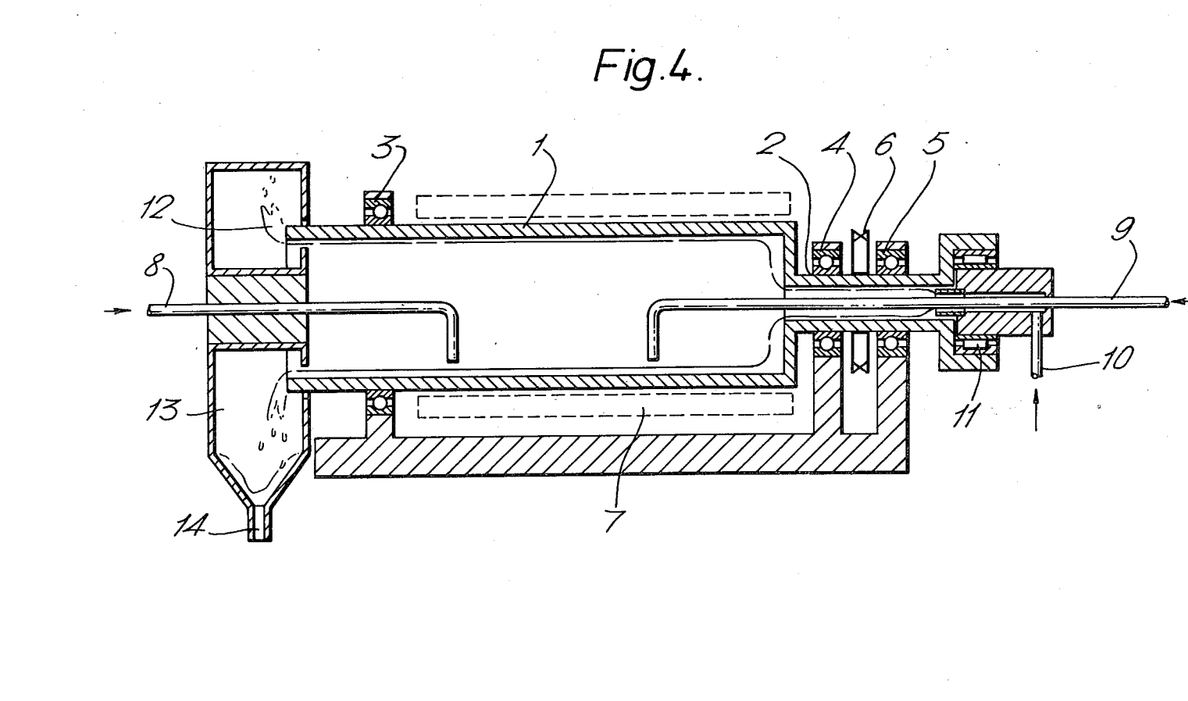
FIG. 4 is a vertical sectional view of a third embodiment of an apparatus in accordance with the present invention.

In order to be able to control the residence time of liquids reacting on the surface of the rotating body and hence the product of the reaction, an apparatus was constructed as shown in FIG. 4.

A long cylindrical tube (1) which narrowed to a smaller bore at (2) was supported on bearings (3, 4, 5) and rotated about a horizontal axis by means of a rotary drive to pulley (6). Heating or cooling of the tube was provided by a jacket (7) and reactants supplied to the interior through any one of three inlet pipes 8, 9, 10. (The inlet pipe 10 conveyed the main liquid reactant supply direct to the internal rotating surface of the tube at the narrow portion 2 through a rotating seal 11). The liquid spread over the surface and moved towards the wider portion of the tube (1) where it was either reacted with other fluids supplied through pipes (8,9) or caused to react by thermal treatment. Movement of the liquid continued whilst the supply was maintained from pipe 10 towards the discharge zone at 12 where the rotation of the tube caused liquid to be sprayed from the rim of the tube into the atmosphere. A collector-housing 13 was supported around the discharge zone of the reaction tube (1) shaped so that liquid drained from the walls thereof and flowed towards an outlet (14) where products were run off and separated. In the apparatus described above and shown in FIG. 4, if liquid of density $\rho$ and viscosity $\mu$ is fed at a volumetric rate of Q onto the surface of a parallel sided tube of length l and radius r rotating about its axis at a rate of f revolutions per unit time, the liquid will be spread into a thin film which travels down the wall of the tube and the residence time is given approximately by the expression:

$$t = \left( \frac{6\pi r^2 \mu l^3}{Q^3 f^2 \rho} \right)^{\frac{1}{3}}$$

The corresponding average film thickness will be $$\frac{Qt}{2\pi r l}$$

which can be calculated if the residence time t is known. The following experiments showed that the formula above for residence time is a useful guide.

(a) Using a tube of radius 4.25 cm and length 100 cm rotated at 3500 rpm silicone oil of 50 poise viscosity was passed down at a feed rate of 110 ml/min and the residence time recorded was 220 secs. A film thickness of 1.5 mm was then calculated from these values using the formula derived above.

(b) Using the same tube and rotation rate, silicone oil of 5 poise was passed down at 280 ml/min giving a residence time of 32 sec and film thickness of 0.6 mm (c) Using the same tube and rotation rate, water of 0.01 poise viscosity was passed down at a rate of 4 4 liters/min giving a residence time 0.9 sec and film thickness of 0.2 mm (d) Using the same tube and flow rate of water, but reducing the rotation rate to 1000 rpm gave a residence time of 1.7 sec and film thickness of 0.4 mm (e) Using a tube of radius 2 cm and length 15 cm rotating at 1000 rpm with a water feed of 400 ml/min the residence time was 1.6 sec and the film thickness 0.6 mm

EXAMPLE 7

Anhydrous ammonia was passed into the reactor described in Examples 4 and 13 through a valve set at 15 psi above atmospheric pressure. An excess of ammonia was maintained throughout the reaction and unreacted gas was vented through a lute system having a hydrostatic pressure of three inches of water. Orthophosphoric acid (65% w/w in water) was pumped into the reactor and fed to the inner surface of the rotating tube at a rate of 24 ml/min. The tube was rotating at a speed of 2600 rpm and a uniform film of phosphoric acid was formed which travelled down the tube in contact with the ammonia gas forming ammonium phosphate products. Although this is an exothermic reaction the temperature was stabilised by the evaporation of water from the surface. The products were flung off the tube in the form of a slurry when they reached the rim, the temperature measured at this point being 93° C.

The slurry flowed into a collecting tank from which it was removed mechanically and dried in a separate rotary evaporator at 50° C. Analysis of the product showed that 74% weight was diammonium orthophosphate and that the ammonia content was 22.4% which indicated that the remainder was mainly mono ammonium orthophosphate.

EXAMPLE 8

A solution of 88% w/w orthophosphoric acid in water was introduced into the reactor described in Examples 4 and 13 at a rate of 20 ml/min whilst the rotating tube was maintained at a speed of 2600 rpm. Excess ammonia gas was passed in continuously as in Example 7 and after the passage of 500 ml of the phosphoric acid solution the reaction products formed were observed to be produced at a stable temperature of 200° C.±10° C. which was maintained as the process continued by rapid evaporation of steam evolved from the surface of the rotating tube. A clear liquor was observed to cover the surface of the tube and travel towards the discharge rim. The liquor was discharged from the tube as a spray and was run into the collector. The product was found by analysis (X-ray diffraction, NMR spectroscopy and titrations) to consist mainly of a melt of mono ammonium ortho phosphate, the di ammonium phosphate presumably having decomposed at the higher discharge temperature in this experiment. The ammonia content of the product was measured as 15% by weight.

EXAMPLE 9

A suspension containing 200 parts basic-lead carbonate added to 500 parts of water was prepared and the particles were kept in suspension by stirring with a simple paddle stirrer. This suspension was pumped onto the rotating reactor surface at a constant rate of 43 ml/min and it was reacted with hydrogen chloride gas, fed into the reactor at a rate of 3.5 liters per minute. The rotating reactor was spun at a rate of 500 rpm and the product of the reaction travelled as a suspension in water towards the rim of the tube where discharge occurred. The temperature of the product was measured to be 55° C. by the thermocouple situated near the discharge zone of the rotating tube. The gases evolved during the reaction and any excess hydrogen chloride were vented from the reactor via a lute having a small hydrostatic pressure ($\simeq$3 inches of water). The solid product after filtering off the aqueous phase was found to be lead chloride ($PbCl_2$).

Conducting this reaction by the process described using a rotating tube has the advantage that the gases evolved (mainly $CO_2$), although they are produced rapidly, can escape into the atmosphere without causing troublesome foaming of the slurry.

EXAMPLE 10

200 parts calcium carbonate were added to 500 parts of water and the solids were suspended by stirring. The slurry was pumped onto the inner surface of the rotating tube of the reactor described in Examples 4 and 13 at a flow rate of 30 mls per minute. The rotational speed of the tube was 500 revs per minute and the hydrogen chloride gas passed into the apparatus at a flow rate of 5 liters per minute. As the slurry reacted on the tube with the hydrogen chloride gas, soluble calcium chloride was formed and the white suspension was observed to change to a colourless liquid as it travelled along the tube. The temperature of the product, a clear solution of calcium chloride was 40° C. as detected by the thermocouple near the discharge zone. No problem with foaming was experienced and the evolved gases were vented via a lute as in Examples 7 and 8.

EXAMPLE 11

Copper carbonate powder was fed near the axis of a curved-sided bowl having a maximum diameter of 6 cm and rotating at 1000 rpm. The particles of powder travelled up the side of the bowl with a residence time of about 20 sec and were flung from the rim and subsequently collected. When the bowl was heated with a jet of air at 400° C. the copper carbonate was quantitatively converted to copper oxide powder on the surface of the bowl as evidenced by a change in colour and the X-ray diffraction pattern of material flung from the rim.

EXAMPLE 12

Benzoic acid in the form of a finely powdered solid was introduced as a continuous stream of particles into a polished stainless steel conically-shaped bowl of half-angle 5° and when the bowl was rotated at high speed (ca. 4000 rpm) the powder, under the influence of centrifugal forces, moved rapidly as a thin layer of material over the surface of the bowl and was flung from the rim. The rotating bowl was enclosed in a vessel into which ammonia gas was pumped and the benzoic acid powder moving on the surface of the bowl was contacted with ammonia gas. An exothermic reaction occurred and ammonium benzoate was formed almost quantitatively before the powder reached the rim. It is likely that reaction of ammonia with benzoic acid takes place initially at the surface of the benzoic acid particles and then the ammonium benzoate first formed becomes detached from the benzoic acid, thus exposing a new surface for further attack by ammonia. This process is probably aided by the abrasion of the particles moving over the surface of the reactor bowl. The ammonium benzoate product collected from the rim of the bowl was a noticeably finer powder than the benzoic acid reactant. The nature of the product was confirmed to be pure ammonium benzoate by IR and NMR spectoscopy.

The exothermic nature of this reaction is moderated on the rotating bowl by rapid heat loss to the surroundings.

If benzoic acid is reacted with ammonia in bulk, hot spots occur and degradation of the ammonium salt to benzamide spoils the purity of the product.

EXAMPLE 13

A small reactor was constructed as shown diagrammatically in FIG. 3. A stainless steel tube (1) is supported and rotated about a vertical axis by a radial spider (2) connecting the tube (1) to a shaft (3) leading to a rotary power unit (4) capable of rotating the tube at speeds up to 20,000 rpm. The power unit (4) is supported on a static casing (5) which is surrounded by a heating jacket (6). The flanged end of the casing (7) is bolted to a collector (8) designed to allow the material discharged from the lower rim (9) of the tube to be continuously collected at (10). Pipes (11, 12, 13) lead from outside the casing to various positions close to the tube (1) and reactants may be fed to the reactor through any of these tubes. Pipe (11) conveys reactant material (solid or liquid) to cone (14) attached to the shaft (3) from which the reactant material will spray off onto the interior surface of the tube (1). Pipes (15) and (16) lead in from the lower part of the casing and these pipes are suitable for introduction and/or venting of gaseous reactants and/or products. All pipes have taps or valves fitted to them but these are not shown on the diagram.

A light source 17 slidable on the inlet tube 15 allows irradiation of any portion of the interior of the reactor tube (1) and hence of reactant materials moving along the surface thereof when the tube is rotated.

EXAMPLE 14

Granules of polymethylmethacrylate were fed from a hopper into the base of a cylindrical jar which was rotating at a speed of 2000 rpm about a vertical axis. The jar was enclosed in an evacuated chamber and was heated by radiant energy to a temperature of 180° C. at the base where the polymer was fed. A few inches above the base another band of radiant heaters heated the jar to a temperature of ca. 325° C.

The polymer granules melted as they contacted the base of the jar and a liquid film of molten polymer moved up the sides of the jar from beneath the mass of solid polymer granules. As the molten polymer film contacted the hotter region rapid de-polymerisation occurred and large quantities of methylmethyacrylate monomer were produced. No polymer climbed to the rim of the jar because it was quantitatively de-polymerised on the way up. The upper region of the tube was cooled with a water jacket and the monomer vapour produced by the polymerisation band lower down condensed on the surface of the upper part of the jar. A film of liquid monomer travelled upwards towards the rim of the jar and was sprayed from the rim by centrifugal force and collected in a moat surrounding the walls of the evacuated chamber.

What we claim is:

1. A process for carrying out a chemical reaction on at least one solid reactant, which comprises: continuously applying the solid reactant in a fluent particulate form to the surface of a rotating body, the surface being a surface of rotation coaxial with the axis of rotation of the body so that forces generated by the rotation of the body cause a film of the reactant to move across the surface from a supply zone to a discharge zone axially remote from the supply zone, heating the moving film of reactant until it melts, effecting the chemical reaction while the reactant moves across the surface as a molten film, regulating the rate of supply of the solid reactant and the speed of rotation of the body such that the product of the reaction is produced during movement of the reactant between the supply and discharge zones, and discharging the product from the surface of rotation at the discharge zone by using the centrifugal force of the rotating body to fling the product from the surface into the surrounding atmosphere.

2. A process as claimed in claim 1 wherein at least a portion of the surface of rotation on which the chemical reaction occurs lies substantially parallel to the axis of rotation.

3. A process as claimed in claim 1 wherein the surface of rotation on which the chemical reaction occurs varies in diameter as it extends in an axial direction.

4. A process as claimed in claim 1 wherein a gaseous product is formed in the reactant medium requiring disengagement from the liquid phase of the reactant medium.

5. A process as claimed in claim 1 wherein a plurality of rotating bodies is used and the product from one is transferred by centrifugal force to another.

6. A process as claimed in claim 1 wherein the surface of rotation and the film of the reactant medium thereupon are irradiated with radiant energy and chemical reaction induced thereby in the said film.

7. A process as claimed in claim 6 wherein the radiation is directed as a beam onto a small region of the film of reactant medium and the rotation of the surface carrying the film causes a greater area of the film to become irradiated.

8. A process as claimed in claim 7 wherein the source of radiation is a laser.

9. A process as claimed in claim 1 which comprises introducing further reactants to the film of reactant medium at a plurality of discrete, axially spaced, positions.

* * * * *